United States Patent [19]
Ihara et al.

[11] Patent Number: 5,565,601
[45] Date of Patent: Oct. 15, 1996

[54] PROCESS FOR PRODUCING PHOSPHORIC ESTERS

[75] Inventors: Takeshi Ihara; Shinji Yano, both of Wakayama; Katsumi Kita, Osaka, all of Japan

[73] Assignee: Kao Corporation, Tokyo, Japan

[21] Appl. No.: 498,697

[22] Filed: Jul. 3, 1995

[30] Foreign Application Priority Data

Jul. 18, 1994 [JP] Japan ................................. 6-165160

[51] Int. Cl.⁶ .................................................. C07F 9/09
[52] U.S. Cl. .................................................. 558/102
[58] Field of Search .............................................. 558/102

[56] References Cited

U.S. PATENT DOCUMENTS 2,938,048  5/1960  Odenweller et al. ................... 558/102
4,714,771  12/1987  Liu .......................................... 558/102

FOREIGN PATENT DOCUMENTS 1-143880  6/1989  Japan .

OTHER PUBLICATIONS

Kagaku Binran, Kiso–hen 2, third revised edition, pp. 338–343, published Jun. 25, 1994.

Primary Examiner—Johann Richter
Assistant Examiner—Michael G. Ambrose
Attorney, Agent, or Firm—Oblon, Spivak, McClelland, Maier & Neustadt, P.C.

[57] ABSTRACT

Phosphoric esters (mono-, di- or triester) is useful as, for example, a cleaner, an emulsifier, an antistatic agent, metal-chelating agent and a lubricant for fibers. It is produced at a high yield while completely trapping the hydrogen chloride gas formed as a by-product. The reaction between a phosphorus oxyhalide and an organic hydroxyl compound to produce a phosphoric ester is effected in the presence of a metal salt of an acid having a pKa of from −5 to 13.

16 Claims, No Drawings

PROCESS FOR PRODUCING PHOSPHORIC ESTERS

FIELD OF THE INVENTION

This invention relates to an improvement in a process for producing phosphoric esters (mono-, di- or triesters). The esters are useful, for example, as cleaners, emulsifiers, antistatic agents and lubricants for fibers.

DESCRIPTION OF RELATED ART

A conventional method for producing a phosphoric ester comprises reacting a phosphorylating agent (for example, phosphorus pentaoxide or polyphosphoric acid) with an organic hydroxyl compound without using any solvent or in an organic solvent, and hydrolyzing the pyrophosphate bond in the reaction mixture. However, purification must be effected in order to obtain a highly pure product by this method. Moreover, it is impossible to produce a phosphoric ester of an organic hydroxyl compound containing, for example, an additional ester functional group or unsaturated bond by this method, since this method is accompanied by, for example, decomposition of the starting material.

There are known methods which use phosphorus oxychloride whereby a phosphoric monoester of high purity can be produced without requiring any step of purification. A method for trapping the hydrogen chloride gas formed by a base is disclosed in JP-A 1-143880 (1989). However, a tertiary amine is used as an HCl-trapping agent in each of these methods. It is not desirable from an industrial viewpoint to use a tertiary amine, which is more expensive than a phosphorus oxyhalide, since the HCl-trapping agent is used not in a catalytic amount but in a stoichiometric amount. Considering the processing of waste water containing an amine and the effects of the amine contaminating the product on human body, it is concluded that such a tertiary amine is not a preferable base from the viewpoint of environmental sanitation. On the other hand, the use of an alkali such as sodium hydroxide as an HCl-trapping agent brings about some problems; for example, the phosphoric ester thus formed is hydrolyzed by water which has been formed as a by-product. It is therefore necessary to develop a low-priced and highly safe HCl-trapping agent as a substitute for these bases.

Description of the Preferred Embodiments of the Invention

Under these circumstances, the present inventors have disclosed that in a process for producing a phosphoric ester (mono-, di- or triester) by reacting a phosphorus oxyhalide with an organic hydroxyl compound, the hydrogen chloride gas formed as a by-product can be completely trapped and the phosphoric ester can be obtained in high yield by effecting the above-mentioned reaction in the presence of a metal salt of an acid having a pKa of from −5 to 13. The present invention has been completed based on this finding.

Accordingly, the present invention provides a process for producing a phosphoric ester by reacting a phosphorus oxyhalide with an organic hydroxyl compound characterized by effecting said reaction in the presence of at least one metal salt of an acid having a pKa of from −5 to 13.

Examples of the phosphorus oxyhalide to be used in the present invention include phosphorus oxychloride and phosphorus oxybromide. Phosphorus oxychloride is a particularly preferable example. Mixtures may be used.

Examples of the organic hydroxyl compound to be used in the present invention include linear or branched, saturated or unsaturated alcohols having 1 to 48 carbon atoms such as methyl alcohol, ethyl alcohol, propyl alcohol, butyl alcohol, pentyl alcohol, hexyl alcohol, 2-ethylhexyl alcohol, heptyl alcohol, octyl alcohol, nonyl alcohol, decyl alcohol, undecyl alcohol, 10-undecen-1-ol, dodecyl alcohol, tridecyl alcohol, tetradecyl alcohol, pentadecyl alcohol, hexadecyl alcohol, heptadecyl alcohol, octadecyl alcohol, oleyl alcohol, elaidyl alcohol, eicosyl alcohol, isostearyl alcohol, higher alcohols obtained by the oxo process, the Ziegler method or the Guerbet method, and alcohols having an ester bond(s) such as glycerol esters such as diglyceride, monoglyceride, alcohols such as polyols such as ethylene glycol, diethylene glycol, propanediol, butanediol and glyceline, and polyether such as poly-(ethylene glycol), polyglyceline, and monosaccharide such as glucose, galactose and fructose, and polysaccharides such as disaccharides, trisaccharides and oligosaccharides or alkylene oxide adducts of these alcohols (the number of moles of the alkylene oxide added: 50 or less), phenol and alkylphenols such as butylphenol, octylphenol, nonylphenol and dodecylphenol, alkylene oxide adducts thereof (the number of moles of the alkylene oxide added: 50 or less), and mixtures of two or more hydroxyl compounds selected from among those cited above.

Among these organic hydroxyl compounds, preferable ones are linear or branched, saturated or unsaturated aliphatic alcohols having 1 to 48 carbon atoms, more preferable ones are alcohols carrying a linear or branched alkyl group having 1 to 32 carbon atoms, and even more preferable ones are alcohols carrying a linear or branched alkyl group having 6 to 20 carbon atoms.

Since hydrochloric acid has a pKa of -8 (Kagaku Binran, Kiso-hen 2, third revised edition, p. 338–342) incorporated herein by reference, it is necessary to select a metal salt of a weaker acid than hydrochloric acid as the HCl-trapping agent to be used in the present invention for trapping the hydrogen gas by-product. Specific examples of such a salt include metal salts of organic and inorganic acids having a pKa of from −5 to 13, preferably from 0 to 11 and more preferably from 2 to 7. All values of pKa and all subranges between these several preferred ranges are specifically included within the present invention pKa values. A metal salt of an acid having a pKa smaller than −5 or exceeding 13 has no ability to trap hydrogen chloride. Thus it is impossible to obtain a colorless phosphoric ester of a high purity at high yield using such a metal salt. Although the metal constituting the metal salt may be any metal, examples thereof are alkali metals (for example, Na and K) and alkaline earth metals (for example, Mg and Ca). It is preferable to use an alkali metal salt.

The pKa value of the invention is that of the original acid. An acid and the corresponding metal salt thereof have the same pKa value as each other as far as it is monovalent.

The acid for a metal salt of an acid used in the present invention is required to have a pKa value ranging between minus 5 to plus 13. The pKa as used herein is disclosed in terms of the critical stability constant as in R. M. Smith, A. E. Martell, "Critical Stability Constants", vol. 4 by Plenum Press in 1976 incorporated herein by reference and can be determined in an aqueous solution thereof at a concentration of 5 millimoles per liter at 25 degree C.

The invention acid of the metal salt preferably includes an organic carboxylic acid, an inorganic acid, and a mixture of the two. The organic carboxylic acid preferably includes a monocarboxylic acid, a polycarboxylic acid having 6 or more carbon atoms and a mixture of the two.

Particular examples of the metal salt having a pKa of from −5 to 13 include metal salts of inorganic acids including borates (e.g., sodium borate (1Na, 2Na and 3Na) and potassium borate (1K, 2K and 3K)), perchlorates such as sodium perchlorate and potassium perchlorate, carbonates and bicarbonates such as potassium carbonate, potassium hydrogencarbonate, sodium carbonate, sodium hydrogencarbonate, magnesium carbonate and calcium carbonate, phosphates such as sodium phosphate (1Na, 2Na and 3Na), potassium phosphate (1K, 2K and 3K), sodium pyrophosphate (1Na, 2Na, 3Na and 4Na), sodium tripolyphosphate (1Na, 2Na, 3Na, 4Na and 5Na), potassium pyrophosphate (1K, 2K, 3K and 4K) and potassium tripolyphosphate (1K, 2K, 3K, 4K and 5K) and sulfates such as sodium sulfate, potassium sulfate, calcium sulfate and magnesium sulfate; and metal salts of organic salts such as sodium, potassium, magnesium and calcium salts of formic acid, acetic acid, propionic acid, acrylic acid, methacrylic acid, adipic acid, aspartic acid, benzoic acid, butyric acid, nicotinic acid, isobutyric acid, octanoic acid, citric acid, glutamic acid, chloroacetic acid, chloropropionic acid, succinic acid, ($C_8$ to $C_{20}$) alkenylsuccinic acid, cyanobenzoic acid, cyanoacetic acid, cyclohexanecarboxylic acid, dichloroacetic acid, oxalic acid, tartaric acid, picolinic acid, vinylacetic acid, phenylacetic acid, fumaric acid, fluoroacetic acid, fluorobenzoic acid, bromobenzoic acid, bromoacetic acid, hexanoic acid, heptanoic acid, phthalic acid, maleic acid, malonic acid, iodoacetic acid, iodobenzoic acid and alkylphosphates, and sodium, potassium, magnesium and calcium salts of homopolymers or copolymers of acrylic acid, methacrylic acid, maleic acid and itaconic acid (examples of comonomers constituting the copolymers include hydrophobic monomers such as styrene, methacrylate and acrylate). Mixtures may be used.

Among these metal salts of organic acids, preferable ones are metal salts of organic carboxylic acids and more preferable ones are metal salts of organic monocarboxylic acids having 1 to 5 carbon atoms in total and optionally substituted with a hydroxyl group. Other preferable ones are sodium and potassium salts of formic acid, acetic acid and propionic acid, and sodium and potassium acetates may be cited as particularly preferable examples thereof. Among these metal salts of inorganic acids, preferable ones include sodium phosphate, sodium carbonate, sodium sulfate and magnesium sulfate.

In the present invention, it is particularly preferable to use a metal salt of an organic monocarboxylic acid having 1 to 5 carbon atoms, for example, sodium acetate or potassium acetate. When such a metal salt of an organic monocarboxylic acid is used, it is preferable to blow a dry gas into the reaction system or to further use a compound capable of absorbing organic monocarboxylic acids to thereby take off the organic monocarboxylic acid (for example, acetic acid) formed as a by-product of the reaction. Examples of compounds capable of absorbing organic monocarboxylic acids include alkali metal salts and alkaline earth metal salts of polycarboxylic acids having 6 or more carbon atoms in total and alkali metal salts and alkaline earth metal salts of inorganic acids such as sulfuric acid and phosphoric acid.

In the present invention, therefore, the most preferable examples of the reaction system include one comprising a combination of a metal salt of an organic monocarboxylic acid having 1 to 5 carbon atoms (for example, acetate) with a metal salt of a polycalboxylic acid having 6 or more carbon atoms in total, and one comprising a combination of a metal salt of an organic monocarboxylic acid having 1 to 5 carbon atoms in total (for example, acetate) with a metal salt of an inorganic acid (for example, sulfate or phosphate). In the system of the combination of a metal salt of an organic monocarboxylic acid having 1 to 5 carbon atoms with a metal salt of a polycarboxylic acid having 6 or more carbon atoms in total, the weight ratio of these constituents (organic monocarboxylic acid salt: polycarboxylic acid salt) preferably ranges from 5:95 to 95:5, more preferably from 30:70 to 80:20, all weight ratios between those limits being expressly included herein. In the system of the combination of a metal salt of an organic monocarboxylic acid having 1 to 5 carbon atoms in total with a metal salt of an inorganic acid, the weight ratio of these constituents (organic monocarboxylic acid salt: inorganic acid salt) preferably ranges from 1:9 to 9:1 including all ranges therebetween.

Preferable examples of the polycarboxylic acid having 6 or more carbon atoms in total to be used herein include sodium, potassium, magnesium and calcium salts of adipic acid, citric acid and ($C_8$ to $C_{20}$) alkenylsuccinic acids and sodium, potassium, magnesium and calcium salts of homopolymers or copolymers of acrylic acid, methacrylic acid, maleic acid and itaconic acid (examples of comonomers constituting the copolymers include hydrophobic monomers such as styrene, methacrylate and acrylate). Further preferable examples thereof include sodium, potassium, magnesium and calcium salts of homopolymers or copolymers of acrylic acid and maleic acid having a molecular weight of 100 to 5,000,000, still preferably 8,000 to 2,000,000.

The amount of metal salt of an acid having a pKa of from −5 to 13 to be added in the present invention generally varies depending on the target phosphoric ester. In order to produce a phosphoric monoester, diester or a triester, it is preferable to add respectively 0.8 to 1.6 mol, 1.6 to 2.8 mol or 1.6 to 3.5 mol, or 2.8 to 4 mol of the metal salt each per mol of the phosphorus oxyhalide including all molar amounts between these limits.

A preferable example of the present invention will be illustrated:

first, a phosphoric monoester may be produced, for example, in accordance with the process of the present invention in the following manner. An organic hydroxyl compound is mixed with a metal salt of an acid having a pKa of from −5 to 13, which is used in an amount of from 0.8 to 1.6 mol (preferably from 0.8 to 1.4 mol) per mol of a phosphorus oxyhalide, without using any solvent or, alternatively, in a solvent such as hexane, heptane, octane, cyclohexane, benzene, toluene, xylene, tetrahydrofuran, chloroform, methylene chloride or diethyl ether. Into the mixture or obtained solution is dropped 1 to 1.2 mol of the phosphorus oxyhalide at a temperature of −30° to 15° C. The mixture is then allowed to react for 0.5 to 4 hours while maintaining the above-mentioned temperature. To the reaction mixture is subsequently added an aqueous solution of an alkali (for example, NaOH or KOH) to give an amount of 3 to 5 equivalents in total (i.e., together with the metal ion of the metal salt added above) per mol of the phosphorus oxyhalide to thereby hydrolyze the P-Cl bond. Then the mixture is stirred at 10° to 60° C. for 0.5 to 1 hour. When it is necessary to further hydrolyze the pyrophosphate bond, an acidic aqueous solution (for example, an aqueous solution of $H_2SO_4$) required for the neutralization of the excessive alkali is added and the resulting mixture is allowed to react at 50° to 100° C. for 0.5 to 3 hours. In this manner a phosphoric monoester can be obtained. Alternatively, a phosphorus oxyhalide may be dropped into a mixture of a solvent and a metal salt followed by the dropping of an organic hydroxyl compound thereinto.

A phosphoric diester may be produced, for example, in the following manner: 2.0 to 2.2 mol of an organic hydroxyl compound and 1.6 to 3.5 mol of a metal salt of an acid having a pKa of from −5 to 13, each per mol of a phosphorus oxyhalide, are mixed together without using any solvent or in such a solvent as those described above. Into the obtained mixture is dropped 1 to 1.1 mol of the phosphorus oxyhalide at −30° to 15° C. Then the mixture is stirred successively at −30° to 15° C. for 0.5 to 4 hours and at 15° to 70° C. for 1 to 10 hours followed by the addition of an aqueous solution of an alkali in an amount required for the hydrolysis of the P-Cl bond. When it is necessary to further hydrolyze the pyrophosphate bond, an acidic aqueous solution (for example, an aqueous solution of $H_2SO_4$) is dropped thereinto. Next the mixture is allowed to react at 50° to 100° C. for 0.5 to 3 hours. Thus a symmetric phosphoric diester can be obtained.

To produce an asymmetric phosphoric diester, 0.8 to 3.5 mol of a metal salt of an acid having a pKa of from −5 to 13 is mixed with such a solvent as those described above and then 1 mol of a phosphorus oxyhalide is dropped thereinto at −30° to 15° C. Subsequently, an organic hydroxyl compound in an amount of 1 mol per mol of the phosphorus oxyhalide is dropped thereinto and the obtained mixture is reacted at −30° to 15° C. for 0.5 to 4 hours. Further, 1 to 1.2 mol of an organic hydroxyl compound different from the above-mentioned one is dropped to the reaction mixture followed by the same treatment as the one employed for producing a symmetric phosphoric diester. Thus an asymmetric phosphoric diester can be obtained.

To produce an asymmetric phosphoric triester, 2.8 to 4 mol of a metal salt of an acid having a pKa of from −5 to 13 is used per mol of a phosphorus oxyhalide and reacted with an organic hydroxyl compound in the same manner as the one employed for the production of an asymmetric phosphoric diester to thereby give an asymmetric diester. Then an organic hydroxyl compound which is either the same or different from those employed in the first and second steps is dropped thereinto and the mixture is reacted at 60° to 80° C. for 2 to 8 hours.

Alternatively, the reactions of the first and second steps may be carried out by using one and the same organic hydroxyl compound and then an organic hydroxyl compound different therefrom may be dropped followed by the reaction at 60° to 80° C. for 2 to 8 hours.

To produce a symmetric phosphoric triester, 2.9 to 3.5 mol of an organic hydroxyl compound and 2.8 to 4 mol of a metal salt of an acid having a pKa of from −5 to 13, each per mol of a phosphorus oxyhalide, are mixed together. Then the phosphorus oxyhalide is dropped thereinto in such a solvent as those described above or without using any solvent and the obtained mixture is reacted at 40° to 80° C. for 2 to 8 hours.

The phosphoric esters produced by the above-mentioned methods are contaminated with by-products such as salts. Although these products may be used as such for some purposes, products having an elevated purity can be obtained by, for example, washing with water or recrystallization, if necessary.

According to the present invention, hydrogen chloride gas, which has been formed as a by-product during the production of a phosphoric ester using phosphorus oxychloride, can be completely trapped by a low-price metal salt of an organic or inorganic acid. This is highly beneficial to the environment and to industry.

The invention will now be explained for them by means of examples which are provided for illustration only and are not limiting of the invention.

EXAMPLES

Example 1 (Synthesis of phosphoric monoester)

Each alcohol and metal salt listed in Table 1 were mixed with 0.8 times by weight as much as the alcohol of hexane (in the case of an alcohol other than those having 10 or less carbon atoms or isostearyl alcohol) or not mixed with hexane (in the case of an alcohol having 10 or less carbon atoms or isostearyl alcohol) and cooled to 5° to 10° C. Into the obtained solution was dropped phosphorus oxychloride in an equivalent amount to the alcohol while maintaining the reaction mixture at the above-mentioned temperature. After the completion of the addition, the mixture was held and aged at 10° C. for 2 to 6 hours. After the completion of the reaction, an appropriate amount of a 48% aqueous solution of sodium hydroxide was added thereto and the mixture was stirred at 40° C. for 30 minutes. Then an appropriate amount of sulfuric acid was added and the mixture was stirred at 90° C. for 3 hours while distilling off the hexane. After adding hexane in an amount of 0.8 times by weight as much as the alcohol, the mixture was divided into layers and washed with water. Then the hexane layer was taken out and the hexane was distilled off to thereby give a phosphoric monoester (MAP). Table 1 shows the kind of alcohols and metal salts employed, the amounts thereof and the amounts (yields) and purities of the MAP products.

TABLE 1

| No. | Alcohol/amount (g) | | Metal salt/amount (g) | | MAP yielded (g)/yield (%) | MAP purity (%) |
|---|---|---|---|---|---|---|
| 1 | 2-ethylhexanol | 80 | sodium acetate | 60 | 128  99 | 97 |
| 2 | dodecanol | 90 | potassium acetate | 57 | 129  99 | 97 |
| 3 | isostearyl alcohol | 90 | $Na_2HPO_4$ | 57 | 115  98 | 98 |
| 4 | 2-(1,3,3-trimethyl-butyl)-5,7,7-tri-methyloctanol | 50 | $Na_2HPO_4$<br>sodium acetate | 16<br>9 | 64  98 | 99 |
| 5 | 2-heptylundecanol | 50 | $Na_2HPO_4$<br>sodium acetate | 11<br>15 | 64  98 | 99 |
| 6 | rapeseed oil diglyceride | 50 | sodium acetate<br>sodium citrate | 6<br>7 | 53  97 | 99 |
| 7 | isostearyl alcohol | 90 | $Na_2CO_3$ | 42 | 115  98 | 98 |
| 8 | 10-undecen-1-ol | 90 | sodium acetate<br>$Na_2HPO_4$ | 43<br>30 | 130  98 | 99 |
| 9 | isostearyl alcohol | 90 | sodium acetate<br>polysodium acrylate (Mw: 10,000) | 27<br>12 | 115  98 | 99 |
| 10 | dodecanol | 90 | sodium acetate | 40 | 129  99 | 99 |

TABLE 1-continued

| No. | Alcohol/amount (g) | | Metal salt/amount (g) | | MAP yielded (g)/yield (%) | MAP purity (%) |
|---|---|---|---|---|---|---|
| 11 | isostearyl alcohol | 90 | MgSO$_4$<br>sodium acetate | 29<br>28 | 115 | 98 | 99 |
| 12 | dodecanol | 90 | MgSO$_4$<br>sodium acetate | 20<br>40 | 129 | 99 | 99 |
| 13 | isostearyl alcohol | 90 | Na$_2$SO$_4$<br>sodium acetate<br>Na$_2$SO$_4$ | 51<br>28<br>36 | 115 | 99 | 99 |

Note: row 11 shows MAP yielded 115/98 with purity 99; row 12 shows 129/99 purity 99; row 13 shows 115/99 purity 99.

Example 2 (Synthesis of symmetric phosphoric diester)

Each alcohol and metal salt listed in Table 2 were mixed with 0.8 times by weight as much hexane as the alcohol (in the case of an alcohol other than those having 10 or less carbon atoms or isostearyl alcohol) or not mixed with hexane (in the case of an alcohol having 10 or less carbon atoms or isostearyl alcohol) and cooled to 5° to 10° C. Into the obtained solution was dropped phosphorus oxychloride in an amount of a ½ equivalent to the alcohol while maintaining the reaction mixture at the above-mentioned temperature. After the completion of the addition, the mixture was stirred at 10° C. for 1 hour and then at room temperature for 10 hours. After the completion of the reaction, an appropriate amount of a 48% aqueous solution of sodium hydroxide was added thereto and the mixture was stirred at 40° C. for 30 minutes. Then ion-exchanged water and sulfuric acid, each in an appropriate amount, were added and the mixture was stirred at 90° C. for 2 hours while distilling off the hexane. After the completion of the stirring, hexane was added in an amount of 0.8 times by weight as much as the alcohol and the mixture was divided into layers and washed with water. Then the hexane was distilled off to give a symmetric phosphoric diester (DAP). Table 2 shows the kinds of alcohols and metal salts employed, the amounts thereof and the amounts (yields) and purities of the DAP products.

Example 3 (Synthesis of asymmetric phosphoric diester)

Each alcohol and metal salt listed in Table 3 were mixed with 2 times by weight as much hexane as the alcohol and the mixture was cooled to 5° to 10° C. Into the obtained solution was dropped phosphorus oxychloride in the equivalent amount to the alcohol of the first step. Next, the alcohol of the first step as shown in Table 3 was dropped thereinto and the mixture was stirred at 10° C. for 1 hour. Then the alcohol of the second step as shown in Table 3 was further dropped thereinto in the equivalent amount to the alcohol of the first step and the mixture was stirred at 60° C. for 3 hours. After the completion of the reaction, an appropriate amount of a 48% aqueous solution of sodium hydroxide was added thereto and the mixture was stirred at 40° C. for 30 minutes. Then ion-exchanged water and sulfuric acid, each in an appropriate amount, were added and the mixture was stirred at 90° C. for 2 hours while distilling off the hexane. After the completion of the stirring, hexane was added in an amount 0.8 times by weight as much as the alcohol and the mixture was divided into layers and washed with water. Then the hexane was distilled off to thereby give an asymmetric phosphoric diester (DAP). Table 3 shows the kinds of alcohols and metal salts employed, the amounts thereof and the amounts (yields) and purities of the DAP products.

TABLE 2

| No. | Alcohol/amount (g) | | Metal salt/amount (g) | | DAP yielded (g)/yield (%) | DAP purity (%) |
|---|---|---|---|---|---|---|
| 1 | hexadecyl alcohol | 100 | sodium acetate | 37 | 110 / 98 | 95 |
| 2 | isostearyl alcohol | 100 | sodium acetate<br>Na$_2$HPO$_4$ | 15<br>37 | 110 / 99 | 98 |
| 3 | 2-ethylhexanol | 100 | Na$_2$HPO$_4$ | 120 | 121 / 98 | 98 |
| 4 | 10-undecen-1-ol | 120 | sodium acetate<br>Na$_2$HPO$_4$ | 29<br>70 | 140 / 99 | 98 |
| 5 | isostearyl alcohol | 100 | sodium acetate<br>polysodium acrylate (Mw: 10,000) | 30<br>17 | 110 / 99 | 98 |
| 6 | isostearyl alcohol | 100 | sodium acetate<br>sodium acrylate/sodium maleate copolymer (Mw: 70,000) | 30<br>20 | 110 / 99 | 98 |
| 7 | isostearyl alcohol | 100 | sodium acetate<br>MgSO$_4$ | 30<br>45 | 110 / 99 | 99 |
| 8 | isostearyl alcohol | 100 | sodium acetate<br>Na$_2$SO$_4$ | 30<br>78 | 110 / 99 | 99 |
| 9 | dodecanol | 100 | sodium acetate<br>MgSO$_4$ | 44<br>32 | 116 / 99 | 99 |
| 10 | dodecanol | 100 | sodium acetate<br>Na$_2$SO$_4$ | 44<br>57 | 116 / 99 | 99 |

TABLE 3

| No. | Alcohol/amount (g) Step 1 | | Step 2 | | Metal salt/amount (g) | | DAP yielded (g)/yield (%) | | DAP purity (%) |
|---|---|---|---|---|---|---|---|---|---|
| 1 | hexadecyl alcohol | 50 | 2-ethylhexanol | 27 | sodium acetate | 41 | 87 | 97 | 95 |
| 2 | isostearyl alcohol | 80 | ethanol | 14 | sodium acetate NaHPO$_4$ | 24 75 | 110 | 98 | 98 |
| 3 | 2-heptylundecanol | 50 | dedecanol | 35 | Na$_2$HPO$_4$ | 63 | 95 | 99 | 98 |
| 4 | 10-undecen-1-ol | 50 | dedecanol | 55 | sodium acetate NaHPO$_4$ | 24 58 | 120 | 98 | 98 |
| 5 | isostearyl alcohol | 80 | ethanol | 14 | sodium acetate polysodium acrylate (Mw: 2000000) | 48 27 | 110 | 98 | 98 |
| 6 | isostearyl alcohol | 80 | ethanol | 14 | sodium acetate MgSO$_4$ | 49 36 | 110 | 98 | 99 |
| 7 | isostearyl alcohol | 80 | ethanol | 14 | sodium acetate Na$_2$SO$_4$ | 49 63 | 110 | 98 | 99 |

Example 4 (Synthesis of symmetric phosphoric triester)

Each alcohol and metal salt listed in Table 4 were mixed with 0.8 times by weight as much hexane as the alcohol (in the case of an alcohol other than those having 10 or less carbon atoms or isostearyl alcohol) or not mixed with hexane (in the case of an alcohol having 10 or less carbon atoms or isostearyl alcohol) and cooled to 5° to 10° C. Into the obtained solution was dropped phosphorus oxychloride in an amount of ⅓.₁ equivalent to the alcohol while maintaining the above-mentioned temperature. After the completion of the addition, the mixture was stirred at 70° C. for 6 hours and then ion-exchanged water was added thereto. After dividing the mixture into layers and washing with water, the hexane was distilled off to thereby give a symmetric phosphoric triester (TAP). Table 4 shows the kinds of alcohols and metal salts employed, the amounts thereof and the amounts (yields) and purities of the TAP products.

dropped thereinto in the equivalent amount to the alcohol of the first step and the mixture was stirred at 60° C. for 6 hours. After adding ion-exchanged water, the mixture was divided into layers and washed with water. Then the hexane was distilled off to thereby give an asymmetric phosphoric triester (TAP).

An asymmetric phosphoric triester, wherein the alcohols of the first and second steps or those of the second and third steps are one and the same, may be synthesized in the following manner too. The products No. 7 to No. 10 given in Table 5 were synthesized by this method.

Namely, when the alcohols used in the first and second steps were one and the same (Nos. 7, 9 and 10), each metal salt and alcohol listed in Table 5 and hexane (twice by weight as much as the alcohol, but not required in the case where the alcohol was a liquid one) were mixed together and cooled to 10° C. Into this solution was dropped phosphorus oxychloride in an amount of ½ equivalent to the alcohol. After the completion of the addition, the mixture was stirred

TABLE 4

| No. | Alcohol/amount (g) | | Metal salt/amount (g) | | TAP yielded (g)/yield (%) | | TAP purity (%) |
|---|---|---|---|---|---|---|---|
| 1 | octanol | 80 | sodium acetate | 61 | 88 | 98 | 92 |
| 2 | 2-ethylhexanol | 80 | sodium acetate Na$_2$HPO$_4$ | 16 75 | 88 | 98 | 98 |
| 3 | isostearyl alcohol | 100 | Na$_2$CO$_3$ | 47 | 103 | 97 | 93 |
| 4 | dodecanol | 70 | potassium acetate | 44 | 75 | 99 | 93 |
| 5 | isostearyl alcohol | 100 | sodium acetate polysodium acrylate (Mw: 2,000,000) | 20 23 | 104 | 98 | 98 |
| 6 | octanol | 80 | sodium acetate MgSO$_4$ | 51 37 | 89 | 99 | 99 |
| 7 | octanol | 80 | sodium acetate Na$_2$SO$_4$ | 51 60 | 89 | 99 | 99 |

Example 5 (Synthesis of asymmetric phosphoric triester)

Each alcohol and metal salt listed in Table 5 were mixed with hexane 2 times by weight as much as the alcohol and the mixture was cooled to 5° to 10° C. To the obtained solution was dropped phosphorus oxychloride in the equivalent amount to the alcohol of the first step. Next, the alcohol of the first step as shown in Table 5 was dropped thereinto and the mixture was stirred at 10° C. for 1 hour. Then the alcohol of the second step as shown in Table 5 was further dropped thereinto in the equivalent amount to the alcohol of the first step and the mixture was stirred at room temperature for 10 hours. Further, the alcohol of the third step was at 10° C. for 3 hours. Further, the alcohol of the third step (1 to 5 equivalents to the phosphorus oxychloride) was added thereto and the mixture was stirred at 10° C. for 1 hour and then at 60° C. for 5 hours. After adding ion-exchanged water and hexane, the mixture was divided into layers and washed with water. Then the hexane was distilled off to thereby give an asymmetric phosphoric triester (TAP).

When the alcohols of the second and third steps were one and the same (No. 8), the alcohol of the first step and the metal salt listed in Table 5 and hexane (twice by weight as much as the alcohol, but not required in the case where the alcohol was a liquid one) were mixed together and cooled to 10° C. Into this solution was dropped phosphorus oxychloride in the equivalent amount to the alcohol of the first step and the mixture was stirred at 10° C. for 1 hour. To the obtained solution was further added the alcohol of the second and third steps (2 to 6 equivalents to the phosphorus oxychloride) and the mixture was stirred at 10° C. for 1 hour and then at 60° C. for 5 hours. After adding ion-exchanged water and hexane, the mixture was divided into layers and washed with water. Then the hexane was distilled off to thereby give an asymmetric phosphoric triester (TAP).

Table 5 shows the kinds of alcohols and metal salts employed, the amounts thereof and the amounts (yields) and purities of the TAP products.

TABLE 5

| No. | Alcohol*1/amount (g) | | Metal salt/amount (g) | | TAP yielded (g)/yield (%) | TAP purity (%) |
|---|---|---|---|---|---|---|
| 1 | (1) isostearyl alcohol | 30 | sodium acetate | 33 | 60  99 | 92 |
|   | (2) dodecanol | 21 | | | | |
|   | (3) ethanol | 5 | | | | |
| 2 | (1) hexadecyl alcohol | 25 | sodium acetate | 9 | 47  99 | 98 |
|   | (2) 2-ethylhexanol | 14 | Na$_2$HPO$_4$ | 38 | | |
|   | (3) ethanol | 5 | | | | |
| 3 | (1) dodecanol | 30 | Na$_2$HPO$_4$ | 82 | 69  98 | 93 |
|   | (2) octanol | 21 | | | | |
|   | (3) butanol | 12 | | | | |
| 4 | (1) dodecanol | 21 | sodium acetate | 9 | 52  99 | 98 |
|   | (2) dodecanol | 21 | Na$_2$HPO$_4$ | 38 | | |
|   | (3) ethanol | 5 | | | | |
| 5 | (1) 2-ethylhexanol | 14 | sodium acetate | 9 | 37  99 | 98 |
|   | (2) 2-ethylhexanol | 14 | Na$_2$HPO$_4$ | | | |
|   | (3) ethanol | 5 | | | | |
| 6 | (1) 10-undecen-1-ol | 19 | sodium acetate | 9 | 50  99 | 98 |
|   | (2) dodecanol | 21 | Na$_2$HPO$_4$ | 38 | | |
|   | (3) ethanol | 5 | | | | |
| 7 | (1) } isostearyl alcohol (2) | 50 | sodium acetate polysodium acrylate (Mw: 10,000) | 15 17 | 57  98 | 98 |
|   | (3) ethanol | 10 | | | | |
| 8 | (1) isostearyl alcohol (2) } ethanol (3) | 50 35 | sodium acetate polysodium acrylate (Mw: 10,000) | 15 52 | 74  98 | 98 |
| 9 | (1) } isostearyl alcohol (2) | 50 | sodium acetate Na$_2$SO$_4$ | 15 19 | 58  99 | 99 |
|   | (3) ethanol | 10 | | | | |
| 10 | (1) } isostearyl alcohol (2) | 50 | sodium acetate MgSO$_4$ | 15 11 | 58  99 | 99 |
|   | (3) ethanol | 10 | | | | |

Note)
*1: (1) means the alcohol added in the first step,
(2) means the one added in the second step and
(3) means the one added in the third step.

Example 6 (Synthesis of symmetric phosphoric diester)

The procedures of Example 2 for synthesizing symmetric phosphoric diesters were repeated except setting the reaction temperature to 15° to 20° C. and using the alcohols and metal salts as listed in Table 6. Thus symmetric phosphoric diesters (DAP) were obtained. Table 6 shows the kinds of alcohols and metal salts employed, the amounts thereof and the amounts (yields) and purities of the DAP products.

TABLE 6

| No. | Alcohol/amount (g) | | Metal salt/amount (g) | | DAP yielded (g)/yield (%) | | DAP purity (%) |
|---|---|---|---|---|---|---|---|
| 1 | isostearyl alcohol | 100 | sodium acetate | 32 | 105 | 95 | 85 |
| 2 | isostearyl alcohol | 100 | sodium acetate<br>$Na_2HPO_4$ | 15<br>37 | 108 | 97 | 94 |
| 3 | isostearyl alcohol | 100 | sodium acetate<br>polysodium acrylate<br>(Mw: 10,000) | 30<br>17 | 110 | 99 | 98 |
| 4 | isostearyl alcohol | 100 | sodium acetate*[1]<br>$MgSO_4$ | 30<br>22 | 110 | 99 | 99 |
| 5 | isostearyl alcohol | 100 | sodium acetate*[1]<br>$Na_2SO_4$ | 30<br>39 | 110 | 99 | 99 |
| 6*[2] | isostearyl alcohol | 100 | sodium acetate | 32 | 106 | 96 | 90 |

Note)
*[1]: aged for 5 hours.
*[2]: the reaction was effected under blowing a dry nitrogen gas at a rate of 50 ml/min.

This application is based on Japanese patent applications 6-165160 filed Jul. 18, 1994 and 7-77556 filed Apr. 3, 1995, both incorporated herein by reference.

What we claim is:

1. A process for producing a phosphoric ester which comprises the step of reacting a phosphorus oxyhalide with an organic hydroxyl compound in the presence of at least one metal salt of an acid having a pKa of from −5 to 13, wherein said metal salt of an acid having a pKa of from −5 to 13 is a metal salt of an organic carboxylic acid.

2. A process for producing a phosphoric ester as set forth in claim 1 wherein said metal salt of an organic carboxylic acid is a metal salt of an organic monocarboxylic acid having 1 to 5 carbon atoms in total which may be substituted with a hydroxyl group.

3. A process for producing a phosphoric ester as set forth in claim 1 wherein said metal salt of an organic carboxylic acid is a mixture of a metal salt of an organic monocarboxylic acid having 1 to 5 carbon atoms in total, which may be substituted with a hydroxyl group, with a metal salt of a polycarboxylic acid having 6 or more carbon atoms in total.

4. A process for producing a phosphoric ester as set forth in claim 2 wherein said metal salt of an organic monocarboxylic acid having 1 to 5 carbon atoms in total, which may be substituted with a hydroxyl group, is a metal acetate.

5. A process for producing a phosphoric ester as set forth in claim 3 wherein said metal salt of a polycarboxylic acid having 6 or more carbon atoms in total is a homopolymer or a copolymer of acrylic acid or maleic acid having a molecular weight of 100 to 5,000,000.

6. A process for producing a phosphoric ester which comprises the step of reacting a phosphorus oxyhalide with an organic hydroxyl compound in the presence of at least one metal salt of an acid having a pKa of from −5 to 13, wherein said metal salt of an acid having a pKa of from −5 to 13 is a mixture of a metal salt of an organic carboxylic acid and a metal salt of an inorganic acid at a weight ratio of from 1:9 to 9:1.

7. A process for producing a phosphoric ester as set forth in claim 4 wherein said metal salt of a polycarboxylic acid having 6 or more carbon atoms in total is a homopolymer or a copolymer of acrylic acid or maleic acid having a molecular weight of 100 to 5,000,000.

8. A process for producing a phosphoric ester as set forth in claim 3 wherein said metal salt of an organic monocarboxylic acid having 1 to 5 carbon atoms in total, which may be substituted with a hydroxyl group, is a metal acetate.

9. The process as claimed in claim 2, wherein said organic hydroxyl compound is a linear or branched, saturated or unsaturated aliphatic alcohol having 1 to 48 carbon atoms.

10. The process as claimed in claim 3, wherein said organic hydroxyl compound is a linear or branched, saturated or unsaturated aliphatic alcohol having 1 to 48 carbon atoms.

11. The process as claimed in claim 4, wherein said organic hydroxyl compound is a linear or branched, saturated or unsaturated aliphatic alcohol having 1 to 48 carbon atoms.

12. The process as claimed in claim 5, wherein said organic hydroxyl compound is a linear or branched, saturated or unsaturated aliphatic alcohol having 1 to 48 carbon atoms.

13. The process as claimed in claim 6, wherein said organic hydroxyl compound is a linear or branched, saturated or unsaturated aliphatic alcohol having 1 to 48 carbon atoms.

14. The process as claimed in claim 1, wherein said organic hydroxyl compound is a linear or branched, saturated or unsaturated aliphatic alcohol having 1 to 48 carbon atoms.

15. The process as claimed in claim 1, wherein said metal salt of an acid having a pKa of from −5 to 13 is used in an amount of from 0.8 to 4 mol per mol of phosphorus oxyhalide.

16. The process as claimed in claim 1, wherein the organic hydroxy compound is a diglyceride.

\* \* \* \* \*